United States Patent
Baumoeller et al.

(10) Patent No.: US 7,622,021 B1
(45) Date of Patent: Nov. 24, 2009

(54) PROCESS FOR PAPER SUBSTRATES USING AN EMULSION AND PRODUCTS PRODUCED THEREBY

(75) Inventors: Guido Baumoeller, Leichlingen (DE); Rolf Kawa, Monheim (DE); Achim Ansmann, Erkrath (DE); Stephan Eichhorn, Gernsheim (DE); Andrea Urban, Ludwigshafen (DE)

(73) Assignee: Cognis IP Management GmbH, Duesseldorf (DE)

( * ) Notice: Subject to any disclaimer, the term of this patent is extended or adjusted under 35 U.S.C. 154(b) by 0 days.

(21) Appl. No.: 09/913,378

(22) PCT Filed: Feb. 4, 2000

(86) PCT No.: PCT/EP00/00904

§ 371 (c)(1),
(2), (4) Date: Nov. 2, 2001

(87) PCT Pub. No.: WO00/47818

PCT Pub. Date: Aug. 17, 2000

(30) Foreign Application Priority Data

Feb. 13, 1999  (DE) ............................... 199 06 081

(51) Int. Cl.
*D21H 21/22* (2006.01)
*D21H 17/60* (2006.01)
*D21H 17/14* (2006.01)

(52) U.S. Cl. .................... 162/158; 162/135; 162/172; 162/179; 424/402; 428/195.1

(58) Field of Classification Search ................. 162/135, 162/179, 158, 172; 424/400–402, 443; 252/8.61–8.63; 428/195.1
See application file for complete search history.

(56) References Cited

U.S. PATENT DOCUMENTS

| | | | |
|---|---|---|---|
| 3,241,968 A | 3/1966 | Garth | |
| 3,653,958 A | 4/1972 | Kohn et al. | |
| 4,172,887 A | 10/1979 | Vanlerberghe et al. | |
| 5,718,891 A | 2/1998 | Prat et al. | |
| 5,730,960 A | 3/1998 | Stein et al. | |
| 5,840,943 A | 11/1998 | Ansmann et al. | |
| 5,871,763 A * | 2/1999 | Luu et al. | 424/402 |
| 5,968,530 A * | 10/1999 | Arquette | 424/401 |
| 6,146,648 A * | 11/2000 | Bret et al. | 424/401 |
| 6,193,960 B1 | 2/2001 | Metzger et al. | |
| 6,207,014 B1 | 3/2001 | de Haut et al. | |
| 6,413,529 B1 * | 7/2002 | Beerse et al. | 424/402 |
| 6,503,412 B1 * | 1/2003 | Schroeder | 252/8.86 |
| 6,562,778 B1 * | 5/2003 | Ansmann et al. | 510/470 |
| 6,623,746 B1 * | 9/2003 | Wadle et al. | 424/402 |
| 6,733,772 B1 * | 5/2004 | Bret et al. | 424/443 |
| 6,797,399 B2 * | 9/2004 | Weuthen et al. | 428/532 |
| 6,797,400 B2 * | 9/2004 | Weuthen et al. | 428/532 |
| 6,860,967 B2 * | 3/2005 | Baumoller et al. | 162/158 |
| 6,905,697 B2 * | 6/2005 | Baumoller et al. | 424/402 |
| 7,285,283 B2 * | 10/2007 | Baumoeller et al. | 424/400 |
| 2002/0146561 A1 * | 10/2002 | Baumoeller et al. | 428/375 |
| 2002/0148583 A1 * | 10/2002 | Baumoeller et al. | 162/158 |
| 2004/0116542 A1 * | 6/2004 | Baumoeller et al. | 516/77 |
| 2004/0234561 A1 * | 11/2004 | Ansmann et al. | 424/401 |
| 2005/0100573 A1 * | 5/2005 | Baumoller et al. | 424/402 |
| 2005/0133180 A1 * | 6/2005 | West et al. | 162/158 |
| 2006/0116524 A1 * | 6/2006 | Bruening et al. | 554/166 |

FOREIGN PATENT DOCUMENTS

| | | |
|---|---|---|
| DE | 1 165 574 | 3/1964 |
| DE | 2 205 467 | 8/1973 |
| DE | 20 24 051 | 5/1986 |
| DE | 43 08 794 | 4/1994 |
| DE | 197 08 133 | 12/1997 |
| DE | 19730423 C1 * | 12/1998 |
| DE | 19805433 A1 * | 8/1999 |
| DE | 19906081 A1 * | 8/2000 |
| EP | 0 693 471 | 1/1996 |
| EP | 0 694 521 | 1/1996 |
| EP | 0 818 450 | 1/1998 |
| EP | 1029977 A1 * | 8/2000 |
| EP | 1225276 A1 * | 7/2002 |
| EP | 1225277 A1 * | 7/2002 |
| EP | 1813311 A1 * | 8/2007 |
| FR | 2252840 | 11/1974 |
| GB | 962919 | 7/1964 |
| GB | 1333475 | 10/1973 |
| WO | WO91/01295 | 2/1991 |
| WO | WO95/16824 | 6/1995 |
| WO | WO95/34528 | 12/1995 |
| WO | WO95/35411 | 12/1995 |
| WO | WO95/35412 | 12/1995 |
| WO | WO97/30216 | 8/1997 |
| WO | WO 9951369 A1 * | 10/1999 |
| WO | WO 01/43715 A1 * | 6/2001 |
| WO | WO 02/056842 A2 * | 7/2002 |

(Continued)

OTHER PUBLICATIONS

Mendiboure et al., "Influence of the intensity of mixing on the droplet size distribution of emulsions: theory and experiment," 1991, Progress in colloid & polymenr Science, vol. 84, pp. 338-341.*

(Continued)

*Primary Examiner*—José A Fortuna

(57) ABSTRACT

A process for making paper substrates having a soft feel involving: (a) providing a paper substrate; (b) providing an emulsion containing: (i) a polyol poly-12-hydroxystearate; (ii) a wax ester; and (iii) a wax; and (c) impregnating the paper substrate with the emulsion.

27 Claims, No Drawings

FOREIGN PATENT DOCUMENTS

| WO | WO 02056841 A2 | * | 7/2002 |
| WO | WO 2007031220 A1 | * | 3/2007 |
| WO | WO 2007059789 A1 | * | 5/2007 |
| WO | WO 2007059888 A2 | * | 5/2007 |

OTHER PUBLICATIONS

Puchta et al., "A New Generation of Softeners," Tenside Surf. Det, vol. 30, pp. 186-191, Carl Hanser Verlag, Munich, 1993.

Brock, M., "Neue Entwicklungen auf dem Gebiet der Wäscheweichspüler," Tenside Surf. Det., vol. 30, pp. 394-399, Carl Hanser Verlag, Munich, 1993.

Lagerman et al., "Synthesis and Performance of Ester Quaternary Biodegradable Softeners;" J. Am. Oil. Chem. Soc., vol. 71, pp. 97-99, 1994.

Shapiro et al., "Environmentally Friendly Ester Quats," Cosm. Toil., vol. 109, pp. 77, 78, 80, (Dec. 1994).

Todd et al., "Volatile Silicone Fluids for Cosmetic Formulations," Cosm. Toil., vol. 91, pp. 29-32, (Jan. 1976).

Tronnier et al., "Experimentelle Untersuchungen zur WIrkungsweise Aluminiumhaltiger Antiperspiranzien," J. Soc. Cosm. Chem., vol. 24, p. 281-290, 1973.

Graham et al., "Inhibition of the Mitochondrial Oxidation of Octanoate by Salicyclic Acid and Related Compounds," J. Pharm. Pharmac, vol. 26, p. 531-534, Hoeschst AG, Frankfurt, 1975.

Finkel, P., "Formulierung Kosmetischer Sonnenschutzmittel," SÖFW-Journal, vol. 122, pp. 543-548, 1996.

"Kosmetische Färbemittel," Farbstoffkommission der Deutschen Forschungsgemeinschaft, Verlag Chemie. Weinheim, pp. 81-106, 1984.

* cited by examiner

PROCESS FOR PAPER SUBSTRATES USING AN EMULSION AND PRODUCTS PRODUCED THEREBY

BACKGROUND OF THE INVENTION

This invention relates generally to utility and hygienic paper towels and, more specifically, to the use of special emulsions as impregnating and softening compositions.

The generic term "paper" encompasses about 3000 different types and articles which can differ, sometimes considerably, in their applications and their properties. Their production involves the use of numerous additives among the most important of which are fillers (for example chalk or kaolin) and binders (for example starch). For tissues and hygienic papers, which come into relatively close contact with the human skin, there is a particular need for an agreeable soft feel which is normally given to the paper by careful selection of the fibers and, in particular, by a high percentage of fresh mechanical wood pulp or cellulose. However, in the interests of economic paper manufacture and from the ecological viewpoint, it is desirable to use large amounts of inferior-quality deinked wastepaper. Unfortunately, this means that the softness of the paper is significantly reduced which is troublesome in practice and can even lead to irritation of the skin, particularly with frequent use.

Accordingly, there has been no shortage of attempts in the past to treat tissue papers by impregnation, coating or other surface treatments in such a way that a more agreeable soft feel is achieved. International patent application WO 95/35411 (Procter & Gamble) relates to tissue papers coated with softening compositions which contain 20 to 80% by weight of a water-free emulsifier (mineral oils, fatty acid esters, fatty alcohol ethoxylates, fatty acid ethoxylates, fatty alcohols and mixtures thereof), 5 to 95% by weight of a carrier (fatty alcohols, fatty acids or fatty alcohol ethoxylates containing 12 to 22 carbon atoms in the fatty group) and 1 to 50% by weight of surfactants with an HLB value of preferably 4 to 20. The Examples mentioned in this document all contain petrolatum as emulsifier. International patent application WO 95/35412 discloses similar tissue papers where water-free mixtures of (a) mineral oils, (b) fatty alcohols or fatty acids and (c) fatty alcohol ethoxylates are used as softeners. International patent application WO 95/16824 (Procter & Gamble) describes softening compositions for tissue papers containing mineral oil, fatty alcohol ethoxylates and nonionic surfactants (sorbitan esters, glucamides). In addition, International patent application WO 97/30216 (Kaysersberg) describes softening compositions for paper handkerchiefs which contain (a) 35 to 90% by weight of long-chain fatty alcohols, (b) 1 to 50% by weight of wax esters containing 24 to 48 carbon atoms, (c) 0 to 20% by weight of nonionic emulsifiers and (d) 0 to 50% by weight of mineral oil. From the applicational standpoint, however, the softness and feel of the treated papers are still in need of improvement.

Accordingly, the problem addressed by the present invention was to provide compositions with which dry utility papers, more particularly tissue papers, and tissue cloths having a particularly agreeable soft feel and excellent skin-care properties could even be produced using raw materials comprising a high percentage of recycled paper. At the same time, only readily biodegradable auxiliaries would be used and the compositions would penetrate easily into the tissue, would be uniformly dispersed therein and, even in highly concentrated form, would have such a low viscosity that they would be easy to process.

DESCRIPTION OF THE INVENTION

The present invention relates to the use of emulsions containing a) polyol poly-12-hydroxystearates, b) wax esters and c) waxes as impregnating and softening compositions for papers, nonwovens and cloths, preferably for treating the skin.

It has surprisingly been found that compositions of the type mentioned above are capable of imparting an agreeable soft feel, even to particularly critical tissue paper comprising up to 95% by weight recycled paper and tissue cloth. The emulsions have low viscosities, even in highly concentrated form, so that they are easy to process. By virtue of their small droplet size, the emulsions penetrate very quickly into the tissues and are uniformly dispersed therein. Another advantage is that the substantially odorless compositions are ecotoxicologically safe and, in particular, are readily biodegradable.

Polyol Poly-12-Hydroxystearates

The polyol poly-12-hydroxystearates which form component (a) are known substances which are marketed by Henkel KGaA of Düsseldorf, FRG, for example under the names of "Dehymuls® PGPH" and "Eumulgin® VL 75" (mixture with Coco Glucosides in a ratio by weight of 1:1). Reference is also made in this connection to International patent application WO 95/34528 (Henkel). The polyol component of the emulsifiers may be derived from substances which contain at least 2, preferably 3 to 12 and more preferably 3 to 8 hydroxyl groups and 2 to 12 carbon atoms. Typical examples are (a) glycerol and polyglycerol;
(b) alkylene glycols such as, for example, ethylene glycol, diethylene glycol, propylene glycol;
(c) methylol compounds such as, in particular, trimethylol ethane, trimethylol propane, trimethylol butane, pentaerythritol and dipentaerythritol;
(d) alkyl oligoglucosides containing 1 to 22, preferably 1 to 8 and more preferably 1 to 4 carbon atoms in the alkyl group such as, for example, methyl and butyl glucoside;
(e) sugar alcohols containing 5 to 12 carbon atoms such as, for example, sorbitol or mannitol,
(f) sugars containing 5 to 12 carbon atoms such as, for example, glucose or sucrose;
(g) amino sugars such as, for example, glucamine.

Among the emulsifiers suitable for use in accordance with the invention, reaction products based on polyglycerol are particularly important by virtue of their excellent applicational properties. It has proved to be of particular advantage to use selected polyglycerols which have the following homolog distribution (the preferred ranges are shown in brackets):

| | |
|---|---|
| glycerol | 5 to 35 (15 to 30) % by weight |
| diglycerols | 15 to 40 (20 to 32) % by weight |
| triglycerols | 10 to 35 (15 to 25) % by weight |
| tetraglycerols | 5 to 20 (8 to 15) % by weight |
| pentaglycerols | 2 to 10 (3 to 8) % by weight |
| oligoglycerols | to 100% by weight |

Wax Esters

Wax esters used as component (b) are generally understood to be substances which correspond to formula (I):

$$R^1COO-R^2 \quad (1)$$

in which $R^1CO$ is a linear or branched acyl group containing 6 to 22 carbon atoms and 0 and/or 1 to 3 double bonds and $R^2$ is a linear or branched alkyl and/or alkenyl group containing 6 to 22 carbon atoms, with the proviso that the number of carbon atoms in the ester is at least 20. Typical examples of such substances are myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Unsaturated wax esters, for example oleyl oleate and oleyl erucate, are preferably used.

Waxes

Waxes which are used as component (c) are natural or synthetic substances which are kneadable at 20° C., solid to fragile and hard, coarsely to finely crystalline, transparent to opaque, but not glass-like, melt without decomposing above 40° C. and are of comparatively low viscosity and non-stringing even just above their melting point. The waxes suitable for use in accordance with the invention differ from resins, for example, in the fact that they change into a molten low-viscosity state at temperatures of generally about 50 to 90° C., in exceptional cases even as high as 200° C., and are substantially free from ash-forming compounds. The waxes are divided into the following three groups according to their origin: natural waxes such as, for example, candelilla wax, carnauba wax, Japan wax, espartograss wax, cork wax, guaruma wax, rice oil wax, sugar cane wax, ouricury wax, montan wax, beeswax, shellac wax, spermaceti, lanolin (wool wax), uropygial fat, ceresine, ozocerite (earth wax), petrolatum, paraffin waxes and microwaxes; chemically modified waxes (hard waxes) such as, for example, montan ester waxes, sasol waxes, hydrogenated jojoba waxes and synthetic waxes such as, for example, polyalkylene waxes and polyethylene glycol waxes. In this connection, natural waxes, especially vegetable waxes, are preferred.

Tissue Papers and Tissue Cloths

Tissue papers to which the present invention relates may have a single-ply or multiple-ply structure. In general, the papers have a weight per square meter of 10 to 65 and preferably 15 to 30 g and a density of 0.6 g/cm³ or lower. Examples of tissue papers to which the use according to the invention is applicable are toilet papers, paper handkerchiefs, facial wipes, make-up removing wipes, freshening wipes, kitchen roll and the like. Depending on the particular application, the tissues may contain special active ingredients, for example moisturizers, insect repellents (after-sun wipes), dihydroxyacetone, deodorizers, surfactants, alcohols (freshening wipes), skin-care oils, anti-inflammatory agents (baby wipes) and the like. Apart from paper-based tissues, the use according to the invention is also applicable to corresponding tissue cloths made of fibers or fleeces.

Emulsions

In one preferred embodiment of the invention, the emulsions contain—again based on active substance content—
(a) 5 to 25, preferably 8 to 20 and more preferably 10 to 15% by weight of polyol poly-12-hydroxystearates,
(b) 50 to 90, preferably 60 to 85 and more preferably 70 to 80% by weight of wax esters and
(c) 5 to 25, preferably 8 to 20 and more preferably 10 to 15% by weight of waxes, with the proviso that the quantities shown add up to 100% by weight. The active substance content of the emulsions may be between 0.5 and 80% by weight according to the particular application envisaged. With relatively high active substance contents, the emulsions undergo a dramatic reduction in flowability; with relatively low active substance contents, they do not develop their intended effect. Concentrates with an active substance content of 10 to 70% by weight which are designed for dilution to an in-use concentration of 1 to 15% by weight are preferably marketed. If desired, the aqueous phase may also contain polyols, preferably up to 15% by weight of glycerol.

Skin-Care Oils

In another preferred embodiment of the invention, skin-care oils are used as auxiliaries and additives. Suitable skin-care oils are, for example, Guerbet alcohols based on fatty alcohols containing 6 to 18 and preferably 8 to 10 carbon atoms, esters of hydroxycarboxylic acids with linear or branched $C_{6-22}$ fatty alcohols, more particularly dioctyl malate, esters of linear and/or branched fatty acids with polyhydric alcohols (for example propylene glycol, dimer diol or trimer triol) and/or Guerbet alcohols, triglycerides based on $C_{6-10}$ fatty acids, liquid mono-/di-/triglyceride mixtures based on $C_{6-18}$ fatty acids, esters of $C_{6-22}$ fatty alcohols and/or Guerbet alcohols with aromatic carboxylic acids, more particularly benzoic acid, esters of $C_{2-12}$ dicarboxylic acids with linear or branched alcohols containing 1 to 22 carbon atoms or polyols containing 2 to 10 carbon atoms and 2 to 6 hydroxyl groups, vegetable oils, branched primary alcohols, substituted cyclohexanes, linear and branched $C_{6-22}$ fatty alcohol carbonates, Guerbet carbonates, esters of benzoic acid with linear and/or branched $C_{6-22}$ alcohols (for example Finsolv® TN), linear or branched, symmetrical or nonsymmetrical dialkyl ethers containing 6 to 22 carbon atoms per alkyl group, ring opening products of epoxidized fatty acid esters with polyols, silicone oils and/or aliphatic or naphthenic hydrocarbons such as, for example, squalane, squalene and dialkylcyclohexanes.

Co-Emulsifiers

If desired, the compositions to be used in accordance with the invention may contain other emulsifiers, preferably nonionic, cationic or amphoteric emulsifiers, such as:

(1) $C_{12/18}$ fatty acid monoesters and diesters of adducts of 1 to 30 moles of ethylene oxide with glycerol;
(2) glycerol mono/diesters, sorbitan mono/diesters and sugar mono/diesters of saturated and unsaturated fatty acids containing 6 to 22 carbon atoms or hydroxycarboxylic acids containing 2 to 6 carbon atoms, for example citric acid, malic acid or tartaric acid, and ethylene oxide adducts thereof;
(3) alkyl mono- and oligoglycosides containing 8 to 22 carbon atoms in the alkyl group and ethoxylated analogs thereof;

(4) adducts of 15 to 60 moles of ethylene oxide with castor oil and/or hydrogenated castor oil;
(5) polyglycerol esters such as, for example, polyglycerol polyricinoleate or polyglycerol dimerate. Mixtures of compounds from several of these classes are also suitable;
(6) adducts of 2 to 15 moles of ethylene oxide with castor oil and/or hydrogenated castor oil;
(7) partial esters based on linear, branched, unsaturated or saturated $C_{6/22}$ fatty acids, ricinoleic acid and 12-hydroxystearic acid and glycerol, polyglycerol, pentaerythritol, dipentaerythritol, sugar alcohols (for example sorbitol), alkyl glucosides (for example methyl glucoside, butyl glucoside, lauryl glucoside) and polyglucosides (for example cellulose);
(8) mono-, di and trialkyl phosphates and mono-, di- and/or tri-PEG-alkyl phosphates and salts thereof;
(9) wool wax alcohols;
(10) polysiloxane/polyalkyl polyether copolymers and corresponding derivatives;
(11) mixed esters of pentaerythritol, fatty acids, citric acid and fatty alcohol according to DE-PS 11 65 574 and/or mixed esters of fatty acids containing 6 to 22 carbon atoms, methyl glucose and polyols, preferably glycerol or polyglycerol,
(12) polyalkylene glycols and
(13) glycerol carbonate.

The addition products of ethylene oxide and/or propylene oxide with glycerol monoesters and diesters and sorbitan monoesters and diesters of fatty acids or with castor oil are known commercially available products. They are homolog mixtures of which the average degree of alkoxylation corresponds to the ratio between the quantities of ethylene oxide and/or propylene oxide and substrate with which the addition reaction is carried out. $C_{12/18}$ fatty acid monoesters and diesters of adducts of ethylene oxide with glycerol are known as refatting agents for cosmetic compositions from DE-PS 20 24 051.

$C_{8/18}$ alkyl mono- and oligoglycosides, their production and their use as surfactants are known from the prior-art literature. They are produced in particular by reacting glucose or oligosaccharides with primary alcohols containing 8 to 18 carbon atoms. So far as the glycoside component is concerned, both monoglycosides where a cyclic sugar unit is attached to the fatty alcohol by a glycoside bond and oligomeric glycosides with a degree of oligomerization of preferably up to about 8 are suitable. The degree of oligomerization is a statistical mean value on which a homolog distribution typical of such technical products is based.

Other suitable emulsifiers are zwitterionic surfactants. Zwitterionic surfactants are surface-active compounds which contain at least one quaternary ammonium group and at least one carboxylate and one sulfonate group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the CTFA name of Cocamidopropyl Betaine is particularly preferred. Ampholytic surfactants are also suitable emulsifiers. Ampholytic surfactants are surface-active compounds which, in addition to a $C_{8/18}$ alkyl or acyl group, contain at least one free amino group and at least one —COOH— or —SO$_3$H— group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-cocoalkylaminopropionate, cocoacylaminoethyl aminopropionate and $C_{12/18}$ acyl sarcosine. According to the invention, other suitable emulsifiers besides ampholytic surfactants are quaternary emulsifiers, those of the esterquat type, preferably methyl-quaternized difatty acid triethanolamine ester salts, being particularly preferred because they further improve softness. "Esterquats" are generally understood to be quaternized fatty acid triethanolamine ester salts. These are known substances which may be obtained by the relevant methods of preparative organic chemistry, cf. International patent application WO 91/01295 (Henkel). According to this document, triethanolamine is partly esterified with fatty acids in the presence of hypophosphorous acid, air is passed through and the reaction product is quaternized with dimethyl sulfate or ethylene oxide. In addition, German patent DE-C1 4308794 (Henkel) describes a process for the production of solid esterquats in which the quaternization of triethanolamine esters is carried out in the presence of suitable dispersants, preferably fatty alcohols. Overviews on this subject have been published, for example, by R. Puchta et al. in Tens. Surf. Det., 30, 186 (1993), by M. Brock in Tens. Surf. Det. 30, 394 (1993), by R. Lagerman et al. in J. Am. Oil. Chem. Soc., 71, 97 (1994) and by I. Shapiro in Cosm. Toil., 109, 77 (1994). The quaternized fatty acid triethanolamine ester salts correspond to formula (II):

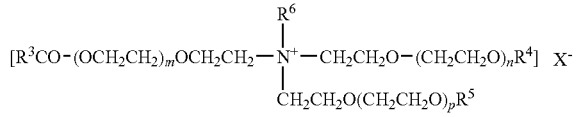

in which $R^3CO$ is an acyl group containing 6 to 22 carbon atoms, $R^4$ and $R^5$ independently of one another represent hydrogen or have the same meaning as $R^3CO$, $R^6$ is an alkyl group containing 1 to 4 carbon atoms or a $(CH_2CH_2O)_qH$ group, m, n and p together stand for 0 or numbers of 1 to 12, q is a number of 1 to 12 and X is halide, alkyl sulfate or alkyl phosphate. Typical examples of esterquats which may be used in accordance with the invention are products based on caproic acid, caprylic acid, capric acid, lauric acid, myristic acid, palmitic acid, isostearic acid, stearic acid, oleic acid, elaidic acid, arachic acid, behenic acid and erucic acid and the technical mixtures thereof obtained for example in the pressure hydrolysis of natural fats and oils. Technical $C_{12/18}$ cocofatty acids and, in particular, partly hydrogenated $C_{16/18}$ tallow or palm oil fatty acids and high-elaidic $C_{16/18}$ fatty acid cuts are preferably used. To produce the quaternized esters, the fatty acids and the triethanolamine may be used in a molar ratio of 1.1:1 to 3:1. With the performance properties of the esterquats in mind, a ratio of 1.2:1 to 2.2:1 and preferably 1.5:1 to 1.9:1 has proved to be particularly advantageous. The preferred esterquats are technical mixtures of mono-, di- and triesters with an average degree of esterification of 1.5 to 1.9 and are derived from technical $C_{16/18}$ tallow or palm oil fatty acid (iodine value 0 to 40). In performance terms, quaternized fatty acid triethanolamine ester salts corresponding to formula (II), in which $R^3CO$ is an acyl group containing 16 to 18 carbon atoms, $R^4$ has the same meaning as $R^3CO$, $R^5$ is hydrogen, $R^6$ is a methyl group, m, n and p stand for 0 and X stands for methyl sulfate, have proved to be particularly advantageous. Other suitable esterquats besides the quaternized fatty acid triethanolamine ester salts are quaternized ester salts of fatty acids with diethanolalkylamines corresponding to formula (III):

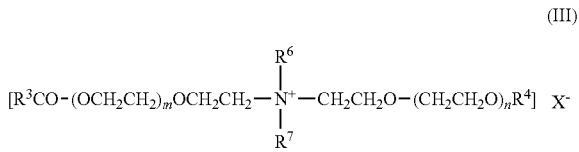

(III)

in which $R^3CO$ is an acyl group containing 6 to 22 carbon atoms, $R^4$ is hydrogen or has the same meaning as $R^3CO$, $R^6$ and $R^7$ independently of one another are alkyl groups containing 1 to 4 carbon atoms, m and n together stand for 0 or numbers of 1 to 12 and X stands for halide, alkyl sulfate or alkyl phosphate. Finally, another group of suitable esterquats are the quaternized ester salts of fatty acids with 1,2-dihydroxypropyl dialkylamines corresponding to formula (IV):

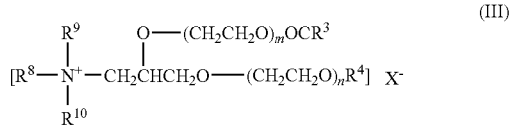

(III)

in which $R^3CO$ is an acyl group containing 6 to 22 carbon atoms, $R^4$ is hydrogen or has the same meaning as $R^3CO$, $R^8$, $R^9$ and $R^{10}$ independently of one another are alkyl groups containing 1 to 4 carbon atoms, m and n together stand for 0 or numbers of 1 to 12 and X stands for halide, alkyl sulfate or alkyl phosphate. So far as the choice of the preferred fatty acids and the optimum degree of esterification is concerned, the examples mentioned in regard to (II) also apply to the esterquats of formulae (III) and (IV).

Active Substances

In one particular embodiment of the invention, the emulsions contain active substances such as, for example, mild surfactants, superfatting agents, consistency factors, thickeners, polymers, silicone compounds, fats, waxes, stabilizers, biogenic agents, deodorizers, film formers, UV protection factors, antioxidants, hydrotropes, preservatives, insect repellents, self-tanning agents, solubilizers, perfume oils, dyes, germ inhibitors and the like.

Typical examples of suitable mild, i.e. dermatologically compatible, surfactants, are fatty alcohol polyglycol ether sulfates, monoglyceride sulfates, mono- and/or dialkylsulfosuccinates, fatty acid isethionates, fatty acid sarcosinates, fatty acid taurides, fatty acid glutamates, α-olefin sulfonates, ether carboxylic acids, alkyl oligoglucosides, fatty acid glucamides, alkyl amidobetaines and/or protein fatty acid condensates (preferably based on wheat proteins).

Superfatting agents may be selected from such substances as, for example, lanolin and lecithin and also polyethoxylated or acylated lanolin and lecithin derivatives, polyol fatty acid esters, monoglycerides and fatty acid alkanolamides, the fatty acid alkanolamides also serving as foam stabilizers.

The consistency factors mainly used are fatty alcohols or hydroxyfatty alcohols containing 12 to 22 and preferably 16 to 18 carbon atoms and also partial glycerides, fatty acids or hydroxyfatty acids. A combination of these substances with alkyl oligoglucosides and/or fatty acid N-methyl glucamides of the same chain length and/or polyglycerol poly-12-hydroxystearates is preferably used. Suitable thickeners are, for example, Aerosil types (hydrophilic silicas), polysaccharides, more especially xanthan gum, guar-guar, agar-agar, alginates and tyloses, carboxymethyl cellulose and hydroxyethyl cellulose, also relatively high molecular weight polyethylene glycol monoesters and diesters of fatty acids, polyacrylates (for example Carbopols® [Goodrich] or Synthalens® [Sigma]), polyacrylamides, polyvinyl alcohol and polyvinyl pyrrolidone, surfactants such as, for example, ethoxylated fatty acid glycerides, esters of fatty acids with polyols, for example pentaerythritol or trimethylol propane, narrow-range fatty alcohol ethoxylates or alkyl oligoglucosides and electrolytes, such as sodium chloride and ammonium chloride.

Suitable cationic polymers are, for example, cationic cellulose derivatives such as, for example, the quaternized hydroxyethyl cellulose obtainable from Amerchol under the name of Polymer JR 400®, cationic starch, copolymers of diallyl ammonium salts and acrylamides, quaternized vinyl pyrrolidone/vinyl imidazole polymers such as, for example, Luviquat® (BASF), condensation products of polyglycols and amines, quaternized collagen polypeptides such as, for example, Lauryldimonium Hydroxypropyl Hydrolyzed Collagen (Lamequat® L/Grünau), quaternized wheat polypeptides, polyethyleneimine, cationic silicone polymers such as, for example, Amodimethicone, copolymers of adipic acid and dimethylaminohydroxypropyl diethylenetriamine (Cartaretine®/Sandoz), copolymers of acrylic acid with dimethyl diallyl ammonium chloride (Merquat® 550/Chemviron), polyaminopolyamides as described, for example, in FR-A 2 252 840 and crosslinked water-soluble polymers thereof, cationic chitin derivatives such as, for example, quaternized chitosan, optionally in microcrystalline distribution, condensation products of dihaloalkylene, for example dibromobutane, with bis-dialkylamines, for example bis-dimethylamino-1,3-propane, cationic guar gum such as, for example, Jaguar® CBS, Jaguar®C-17, Jaguar® C-16 of Celanese, quaternized ammonium salt polymers such as, for example, Mirapol® A-15, Mirapol® AD-1, Mirapol® AZ-1 of Miranol.

Suitable anionic, zwitterionic, amphoteric and nonionic polymers are, for example, vinyl acetate/crotonic acid copolymers, vinyl pyrrolidone/vinyl acrylate copolymers, vinyl acetate/butyl maleate/isobornyl acrylate copolymers, methyl vinylether/maleic anhydride copolymers and esters thereof, uncrosslinked and polyol-crosslinked polyacrylic acids, acrylamidopropyl trimethylammonium chloride/acrylate copolymers, octylacrylamide/methyl methacrylate/tert.-butylaminoethyl methacrylate/2-hydroxypropyl methacrylate copolymers, polyvinyl pyrrolidone, vinyl pyrrolidone/vinyl acetate copolymers, vinyl pyrrolidone/dimethylaminoethyl methacrylate/vinyl caprolactam terpolymers and optionally derivatized cellulose ethers and silicones.

Suitable silicone compounds are, for example, dimethyl polysiloxanes, methylphenyl polysiloxanes, cyclic silicones and amino-, fatty acid-, alcohol-, polyether-, epoxy-, fluorine-, glycoside- and/or alkyl-modified silicone compounds which may be both liquid and resin-like at room temperature. Other suitable silicone compounds are simethicones which are mixtures of dimethicones with an average chain length of 200 to 300 dimethylsiloxane units and hydrogenated silicates. In addition, a detailed overview of suitable volatile silicones was published by Todd et al. in Cosm. Toil. 91, 27 (1976).

Metal salts of fatty acids such as, for example, magnesium, aluminium and/or zinc stearate or ricinoleate may be used as stabilizers.

In the context of the invention, biogenic agents are, for example, tocopherol, tocopherol acetate, tocopherol palmitate, ascorbic acid, deoxyribonucleic acid, retinol, bisabolol, allantoin, phytantriol, panthenol, AHA acids, amino acids, ceramides, pseudoceramides, essential oils, plant extracts and vitamin complexes.

Suitable deodorizers are, for example, antiperspirants, such as aluminium chlorhydrates. These antiperspirants are colorless hygroscopic crystals which readily deliquesce in air and which accumulate when aqueous aluminium chloride solutions are concentrated by evaporation. Aluminium chlorhydrate is used for the production of perspiration-inhibiting and deodorizing compositions and probably acts by partially blocking the sweat glands through the precipitation of proteins and/or polysaccharides [cf. J. Soc. Cosm. Chem. 24, 281 (1973)]. For example, an aluminium chlorhydrate which corresponds to the formula $[Al_2(OH)_5Cl]*2.5H_2O$ and which is particularly preferred for the purposes of the invention is commercially available under the name of Locron® from Hoechst AG of Frankfurt, FRG [cf. J. Pharm. Pharmcol. 26, 531 (1975)]. Besides the chlorhydrates, aluminium hydroxylactates and acidic aluminium/zirconium salts may also be used. Other suitable deodorizers are esterase inhibitors, preferably trialkyl citrates, such as trimethyl citrate, tripropyl citrate, triisopropyl citrate, tributyl citrate and, in particular, triethyl citrate (Hydagen® CAT, Henkel KGaA, Düsseldorf, FRG). Esterase inhibitors inhibit enzyme activity and thus reduce odor formation. The free acid is probably released through the cleavage of the citric acid ester, reducing the pH value of the skin to such an extent that the enzymes are inhibited. Other esterase inhibitors are sterol sulfates or phosphates, for example lanosterol, cholesterol, campesterol, stigmasterol and sitosterol sulfate or phosphate, dicarboxylic acids and esters thereof, for example glutaric acid, glutaric acid monoethyl ester, glutaric acid diethyl ester, adipic acid, adipic acid monoethyl ester, adipic acid diethyl ester, malonic acid and malonic acid diethyl ester, hydroxycarboxylic acids and esters thereof, for example citric acid, malic acid, tartaric acid or tartaric acid diethyl ester. Antibacterial agents which influence the germ flora and destroy or inhibit the growth of perspiration-decomposing bacteria, may also be present in stick products. Examples of such antibacterial agents are chitosan, phenoxyethanol and chlorhexidine gluconate. 5-Chloro-2-(2,4-dichlorophenoxy)phenol, which is marketed under the name of Irgasan® by Ciba-Geigy of Basel, Switzerland, has also proved to be particularly effective.

UV protection factors in the context of the invention are, for example, organic substances (light filters) which are liquid or crystalline at room temperature and which are capable of absorbing ultraviolet radiation and of releasing the energy absorbed in the form of longer-wave radiation, for example heat. UV-B filters can be oil-soluble or water-soluble. The following are examples of oil-soluble substances:

- 3-benzylidene camphor or 3-benzylidene norcamphor and derivatives thereof, for example 3-(4-methylbenzylidene)-camphor as described in EP-B1 0693471;
- 4-aminobenzoic acid derivatives, preferably 4-(dimethylamino)-benzoic acid-2-ethylhexyl ester, 4-(dimethylamino)-benzoic acid-2-octyl ester and 4-(dimethylamino)-benzoic acid amyl ester;
- esters of cinnamic acid, preferably 4-methoxycinnamic acid-2-ethylhexyl ester, 4-methoxycinnamic acid propyl ester, 4-methoxycinnamic acid isoamyl ester, 2-cyano-3,3-phenylcinnamic acid-2-ethylhexyl ester (Octocrylene);
- esters of salicylic acid, preferably salicylic acid-2-ethylhexyl ester, salicylic acid-4-isopropylbenzyl ester, salicylic acid homomethyl ester;
- derivatives of benzophenone, preferably 2-hydroxy-4-methoxybenzophenone, 2-hydroxy-4-methoxy-4'-methylbenzophenone, 2,2'-dihydroxy-4-methoxybenzophenone;
- esters of benzalmalonic acid, preferably 4-methoxybenzalmalonic acid di-2-ethylhexyl ester;
- triazine derivatives such as, for example, 2,4,6-trianilino-(p-carbo-2'-ethyl-1'-hexyloxy)-1,3,5-triazine and Octyl Triazone as described in EP-A1 0818450;
- propane-1,3-diones such as, for example, 1-(4-tert.butylphenyl)-3-(4'-methoxyphenyl)-propane-1,3-dione;
- ketotricyclo(5.2.1.0)decane derivatives as described in EP-B1 0694521.

Suitable water-soluble substances are

- 2-phenylbenzimidazole-5-sulfonic acid and alkali metal, alkaline earth metal, ammonium, alkylammonium, alkanolammonium and glucammonium salts thereof;
- sulfonic acid derivatives of benzophenones, preferably 2-hydroxy-4-methoxybenzophenone-5-sulfonic acid and salts thereof;
- sulfonic acid derivatives of 3-benzylidene camphor such as, for example, 4-(2-oxo-3-bornylidenemethyl)-benzene sulfonic acid and 2-methyl-5-(2-oxo-3-bornylidene)-sulfonic acid and salts thereof.

Typical UV-A filters are, in particular, derivatives of benzoyl methane such as, for example, 1-(4'-tert.butylphenyl)-3-(4'-methoxyphenyl)-propane-1,3-dione, 4-tert.butyl-4'-methoxydibenzoyl methane (Parsol 1789) or 1-phenyl-3-(4'-isopropylphenyl)-propane-1,3-dione. The UV-A and UV-B filters may of course also be used in the form of mixtures. Besides the soluble substances mentioned, insoluble light-blocking pigments, i.e. finely dispersed metal oxides or salts, may also be used for this purpose. Examples of suitable metal oxides are, in particular, zinc oxide and titanium dioxide and also oxides of iron, zirconium oxide, silicon, manganese, aluminium and cerium and mixtures thereof. Silicates (talcum), barium sulfate and zinc stearate may be used as salts. The oxides and salts are used in the form of the pigments for skin-care and skin-protecting emulsions and decorative cosmetics. The particles should have a mean diameter of less than 100 nm, preferably between 5 and 50 nm and more preferably between 15 and 30 nm. They may be spherical in shape although ellipsoidal particles or other non-spherical particles may also be used. The pigments may also be surface-treated, i.e. hydrophilized or hydrophobicized. Typical examples are coated titanium dioxides, for example Titandioxid T 805 (Degussa) and Eusolex® T2000 (Merck). Suitable hydrophobic coating materials are, above all, silicones and, among these, especially trialkoxyoctylsilanes or simethicones. So-called micro- or nanopigments are preferably used in sun protection products. Micronized zinc oxide is preferably used. Other suitable UV filters can be found in P. Finkel's review in SOFW-Journal 122, 543 (1996).

Besides the two groups of primary sun protection factors mentioned above, secondary sun protection factors of the antioxidant type may also be used. Secondary sun protection factors of the antioxidant type interrupt the photochemical reaction chain which is initiated when UV rays penetrate into the skin. Typical examples are amino acids (for example glycine, histidine, tyrosine, tryptophane) and derivatives thereof, imidazoles (for example urocanic acid) and derivatives thereof, peptides, such as D,L-carnosine, D-carnosine, L-carnosine and derivatives thereof (for example anserine), carotinoids, carotenes (for example α-carotene, β-carotene, lycopene) and derivatives thereof, chlorogenic acid and derivatives thereof, liponic acid and derivatives thereof (for example dihydroliponic acid), aurothioglucose, propylthiouracil and other thiols (for example thioredoxine, glutathione, cysteine, cystine, cystamine and glycosyl, N-acetyl, methyl, ethyl, propyl, amyl, butyl and lauryl, palmitoyl, oleyl, γ-linoleyl, cholesteryl and glyceryl esters thereof) and their salts, dilaurylthiodipropionate, distearylthiodipropionate, thiodipropionic acid and derivatives thereof (esters, ethers, peptides, lipids, nucleotides, nucleosides and salts) and sulfoximine compounds (for example butionine sulfoximines, homocysteine sulfoximine, butionine sulfones, penta-, hexa- and hepta-thionine sulfoximine) in very small compatible dosages (for example pmole to μmole/kg), also (metal) chelators (for example α-hydroxyfatty acids, palmitic acid, phytic acid, lactoferrine), α-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof (for example γ-linolenic acid, linoleic acid, oleic acid), folic acid and derivatives thereof, ubiquinone and ubiquinol and derivatives thereof, vitamin C and derivatives thereof (for example ascorbyl palmitate, Mg ascorbyl phosphate, ascorbyl acetate), tocopherols and derivatives (for example vitamin E acetate), vitamin A and derivatives (vitamin A palmitate) and coniferyl benzoate of benzoin resin, rutinic acid and derivatives thereof, α-glycosyl rutin, ferulic acid, furfurylidene glucitol, carnosine, butyl hydroxytoluene, butyl hydroxyanisole, nordihydroguaiac resin acid, nordihydroguairetic acid, trihydroxybutyrophenone, uric acid and derivatives thereof, mannose and derivatives thereof, Superoxid-Dismutase, zinc and derivatives thereof (for example ZnO, $ZnSO_4$), selenium and derivatives thereof (for example selenium methionine), stilbenes and derivatives thereof (for example stilbene oxide, trans-stilbene oxide) and derivatives of these active substances suitable for the purposes of the invention (salts, esters, ethers, sugars, nucleotides, nucleosides, peptides and lipids).

In addition, hydrotropes, for example ethanol, isopropyl alcohol or polyols, may be used to improve flow behavior. Suitable polyols preferably contain 2 to 15 carbon atoms and at least two hydroxyl groups. The polyols may contain other functional groups, more especially amino groups, or may be modified with nitrogen. Typical examples are glycerol;
alkylene glycols such as, for example, ethylene glycol, diethylene glycol, propylene glycol, butylene glycol, hexylene glycol and polyethylene glycols with an average molecular weight of 100 to 1000 dalton;
technical oligoglycerol mixtures with a degree of self-condensation of 1.5 to 10 such as, for example, technical diglycerol mixtures with a diglycerol content of 40 to 50% by weight;
methylol compounds such as, in particular, trimethylol ethane, trimethylol propane, trimethylol butane, pentaerythritol and dipentaerythritol;
lower alkyl glucosides, particularly those containing 1 to 8 carbon atoms in the alkyl group, for example methyl and butyl glucoside;
sugar alcohols containing 5 to 12 carbon atoms, for example sorbitol or mannitol,
sugars containing 5 to 12 carbon atoms, for example glucose or sucrose;
aminosugars, for example glucamine;
dialcoholamines, such as diethanolamine or 2-aminopropane-1,3-diol.

Suitable preservatives are, for example, phenoxyethanol, formaldehyde solution, parabens, pentanediol or sorbic acid and the other classes of compounds listed in Appendix 6, Parts A and B of the Kosmetikverordnung ("Cosmetics Directive"). Suitable insect repellents are N,N-diethyl-m-toluamide, pentane-1,2-diol or Insect Repellent 3535. A suitable self-tanning agent is dihydroxyacetone.

Suitable perfume oils are mixtures of natural and synthetic fragrances. Natural fragrances include the extracts of blossoms (lily, lavender, rose, jasmine, neroli, ylang-ylang), stems and leaves (geranium, patchouli, petitgrain), fruits (anise, coriander, caraway, juniper), fruit peel (bergamot, lemon, orange), roots (nutmeg, angelica, celery, cardamon, costus, iris, calmus), woods (pinewood, sandalwood, guaiac wood, cedarwood, rosewood), herbs and grasses (tarragon, lemon grass, sage, thyme), needles and branches (spruce, fir, pine, dwarf pine), resins and balsams (galbanum, elemi, benzoin, myrrh, olibanum, opoponax). Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, phenoxyethyl isobutyrate, p-tert.butyl cyclohexylacetate, linalyl acetate, dimethyl benzyl carbinyl acetate, phenyl ethyl acetate, linalyl benzoate, benzyl formate, ethylmethyl phenyl glycinate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, lilial and bourgeonal. Examples of suitable ketones are the ionones, α-isomethylionone and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable fragrance. Other suitable perfume oils are essential oils of relatively low volatility which are mostly used as aroma components. Examples are sage oil, chamomile oil, clove oil, melissa oil, mint oil, cinnamon leaf oil, lime-blossom oil, juniper berry oil, vetiver oil, olibanum oil, galbanum oil, labolanum oil and lavendin oil. The following are preferably used either individually or in the form of mixtures: bergamot oil, dihydromyrcenol, lilial, lyral, citronellol, phenylethyl alcohol, α-hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, β-damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillat, irotyl and floramat.

Suitable dyes are any of the substances suitable and approved for cosmetic purposes as listed, for example, in the publication "Kosmetische Färbemittel" of the Farbstoffkommission der Deutschen Forschungsgemeinschaft, Verlag Chemie, Weinheim, 1984, pages 81 to 106. These dyes are normally used in concentrations of 0.001 to 0.1% by weight, based on the mixture as a whole.

Typical examples of germ inhibitors are preservatives which act specifically against gram-positive bacteria such as, for example, 2,4,4'-trichloro-2'-hydroxydiphenyl ether, chlorhexidine (1,6-di-(4-chlorophenylbiguanido)-hexane) or TCC (3,4,4'-trichlorocarbanilide). Numerous perfumes and essential oils also have antimicrobial properties. Typical examples are the active substances eugenol, menthol and thymol in nettle, mint and thyme oil. An interesting natural deodorant is the terpene alcohol farnesol (3,7,11-trimethyl-2,6,10-dodecatrien-1-ol) which is present in linden blossom oil and which smells of lily-of-the-valley. Glycerol monolaurate has also been successfully used as a bacteriostatic agent. The percentage content of the additional germ inhibitors is normally about 0.1 to 2% by weight, based on the solids component of the formulations.

The total percentage content of auxiliaries and additives may be from 1 to 50% by weight and is preferably from 5 to 40% by weight, based on the particular composition. The compositions may be produced by standard hot or cold processes and are preferably produced by the phase inversion temperature method.

Treatment of the Tissue Papers with the Softening Compositions

The treatment of the tissue papers with the softening compositions may be carried out in known manner, the solution being applied to at least one side of the papers. Basically, any known method by which liquids or melts can be applied to more or less hard surfaces may be used for this purpose, including for example spraying, printing (for example flexographic printing), coating (gravure coating), extrusion and combinations of these methods. The papers/tissues may also be impregnated with the compositions. Application of the compositions is generally followed by a brief drying step. Processes for treating tissue papers with softening compositions are described in detail in the above-cited documents WO 95/35411 and WO 97/30216 to which reference is hereby specifically made.

EXAMPLES

To test performance properties, commercially available three-ply tissue papers with a recycled paper content of 95% and a weight of 18 g/m² were treated with emulsions 1 to 5 according to the invention and with the two comparison compositions C1 and C2 in quantities of 2.5 g/m². The papers were then dried for 30 minutes at 30° C., after which their softness was evaluated by a panel of six experienced testers on a scale of (+++) very soft to (+) hard. The sensorial feeling on touching the tissues was also evaluated. The results which represent the averages of three test series are set out in Table 1.

TABLE 1

Softness of tissue papers using emulsions

| Composition/performance | 1 | 2 | 3 | 4 | 5 | C1 | C2 |
|---|---|---|---|---|---|---|---|
| Polyglyceryl-2-Dipolyhydroxystearate | 8.0 | 10.0 | 8.0 | 8.0 | 10.0 | – | – |
| Glyceryl Oleate | – | – | – | – | – | 8.0 | 10.0 |
| Oleyl Erucate | 60.0 | 65.0 | – | – | 55.0 | 60.0 | 65.0 |
| Oleyl Oleate | – | – | 60.0 | – | – | – | – |
| Candelilla wax | 7.0 | 6.0 | – | 65.0 | – | 7.0 | 5.0 |
| Carnauba wax | – | – | 7.0 | 5.0 | – | – | – |
| Bees Wax | – | – | – | – | 5.0 | – | – |
| Water | | | | | to 100 | | |
| Softness | +++ | +++ | +++ | ++ | ++ | + | + |
| Sensorial evaluation | Moist | Moist | Moist | Moist | Moist | Flat | Flat |

The invention claimed is:

1. A process for making paper substrates having a soft feel comprising:
   (a) providing a paper substrate;
   (b) providing an emulsion consisting essentially of:
      (i) about 5 to 25% by weight of a polyol poly-12-hydroxystearate, based on the weight of the emulsion;
      (ii) about 70 to 80% by weight of a wax ester, based on the weight of the emulsion; and
      (iii) about 5 to 25% by weight of a wax, based on the weight of the emulsion, said emulsion being of a droplet size effective to uniformly penetrate said paper substrate; and
   (c) impregnating the paper substrate with the emulsion, wherein said emulsion penetrates into said paper substrate and is uniformly dispersed therein.

2. The process of claim 1 wherein the polyol poly-12-hydroxystearate is polyglycerol poly-12-hydroxystearate.

3. The product of the process of claim 2.

4. The process of claim 2 wherein said polyglycerol poly-12-hydroxystearate is present in the emulsion in an amount of about 10% by weight.

5. The process of claim 2 wherein said polyglycerol poly-12-hydroxystearate is present in the emulsion in an amount of about 8% by weight.

6. The process of claim 1 wherein the wax ester corresponds to formula (I):

$$R^1COO\text{—}R^2 \quad (1)$$

wherein $R^1CO$ is a linear or branched acyl group having from 6 to 22 carbon atoms and up to 3 double bonds, and $R^2$ is a linear or branched alkyl and/or alkenyl group having from 6 to 22 carbon atoms, and wherein the total number of carbon atoms present in the ester is at least 20.

7. The product of the process of claim 6.

8. The process of claim 1 wherein the paper substrate is based on up to about 95% by weight recycled paper pulp.

9. The product of the process of claim 8.

10. The product of the process of claim 1.

11. The process of claim 1 wherein the polyol poly-12-hydroxystearate is polyethylene glycol poly-12-hydroxystearate.

12. The product of the process of claim 11.

13. The process of claim 1 wherein the polyol contains from 2 to 12 hydroxyl groups and from 2 to 12 carbon atoms.

14. The product of the process of claim 13.

15. A process for making paper substrates having a soft feel comprising:
   (a) providing a paper substrate;
   (b) providing an emulsion consisting essentially of:
      (i) about 5 to 25% by weight of a polyol poly-12-hydroxystearate, based on the weight of the emulsion;
      (ii) about 70 to 80% by weight of an unsaturated wax ester, based on the weight of the emulsion; and
      (iii) about 5 to 25% by weight of a wax, based on the weight of the emulsion, said emulsion being of a droplet size effective to uniformly penetrate said paper substrate; and
   (c) impregnating the paper substrate with the emulsion, wherein said emulsion penetrates into said paper substrate and is uniformly dispersed therein.

16. The product of the process of claim 15.

17. The process of claim 15 wherein the polyol poly-12-hydroxystearate is polyglycerol poly-12-hydroxystearate.

18. The process of claim 15 wherein the unsaturated wax ester is selected from the group consisting of glycerol oleate, oleyl erucate, oleyl oleate and mixtures thereof.

19. A process for making moist paper substrates having a soft feel comprising:
 (a) providing a paper substrate;
 (b) providing an emulsion consisting essentially of:
  (i) about 5 to 25% by weight of a polyol poly-12-hydroxystearate, based on the weight of the emulsion;
  (ii) about 70 to 80% by weight of an unsaturated wax ester, based on the weight of the emulsion; and
  (iii) about 5 to 25% by weight of a wax, based on the weight of the emulsion, said emulsion being of a droplet size effective to uniformly penetrate said paper substrate; and
 (c) impregnating the paper substrate with the emulsion, wherein said emulsion penetrates into said paper substrate and is uniformly dispersed therein.

20. The process of claim 19, wherein the polyol poly-12-hydroxystearate is polyglycerol poly-12-hydroxystearate.

21. The product of the process of claim 20.

22. The process of claim 19, wherein the unsaturated wax ester is selected from the group consisting of glycerol oleate, oleyl erucate, oleyl oleate and mixtures thereof.

23. A process for making moist paper substrates having a soft feel comprising:
 (a) providing a paper substrate;
 (b) providing an emulsion consisting essentially of:
  (i) about 5 to 25% by weight of a polyol poly-12-hydroxystearate, based on the weight of the emulsion;
  (ii) about 70 to 80% by weight of an unsaturated wax ester selected from the group consisting of glycerol oleate, oleyl erucate, oleyl oleate and mixtures thereof, based on the weight of the emulsion; and
  (iii) about 5 to 25% by weight of a wax, based on the weight of the emulsion, said emulsion being of a droplet size effective to uniformly penetrate said paper substrate; and
 (c) impregnating the paper substrate with the emulsion, wherein said emulsion penetrates into said paper substrate and is uniformly dispersed therein.

24. The process of claim 23, wherein the polyol poly-12-hydroxystearate is polyglycerol poly-12-hydroxystearate.

25. The process of claim 2 wherein said polyglycerol poly-12-hydroxystearate is present in the emulsion in an amount of from about 8% to about 10% by weight of the emulsion.

26. The product of the process of claim 25.

27. The process of claim 25 wherein said wax ester is present in the emulsion in an amount of from about 55% to about 65% by weight of the emulsion and said wax is present in the emulsion in an amount of from about 6% to about 7% of the emulsion.

* * * * *